(12) United States Patent
Buschke et al.

(10) Patent No.: US 11,167,100 B2
(45) Date of Patent: *Nov. 9, 2021

(54) ANESTHESIA VENTILATOR FOR THE AUTOMATED VENTILATION OF A PATIENT

(71) Applicant: Drägerwerk AG & Co. KGaA, Lübeck (DE)

(72) Inventors: Wilfried Buschke, Lübeck (DE); Christoph Hörmann, Mank (AT); Stefan Mersmann, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 700 days.

This patent is subject to a terminal disclaimer.

(21) Appl. No.: 15/780,438

(22) PCT Filed: Nov. 21, 2016

(86) PCT No.: PCT/EP2016/001952
§ 371 (c)(1),
(2) Date: May 31, 2018

(87) PCT Pub. No.: WO2017/137055
PCT Pub. Date: Aug. 17, 2017

(65) Prior Publication Data
US 2018/0369525 A1 Dec. 27, 2018

(30) Foreign Application Priority Data
Dec. 2, 2015 (DE) .................. 10 2015 015 440.0

(51) Int. Cl.
*A61M 16/00* (2006.01)
*A61M 16/01* (2006.01)
(Continued)

(52) U.S. Cl.
CPC .......... *A61M 16/024* (2017.08); *A61B 5/082* (2013.01); *A61B 5/4821* (2013.01);
(Continued)

(58) Field of Classification Search
CPC .............. A61M 16/00; A61M 16/0003; A61M 16/0051; A61M 16/01; A61M 16/024;
(Continued)

(56) References Cited

U.S. PATENT DOCUMENTS 5,094,235 A * 3/1992 Westenskow ....... A61M 16/104
128/204.22
5,235,971 A * 8/1993 Falb ...................... A61M 16/18
128/203.12
(Continued)

FOREIGN PATENT DOCUMENTS

DE 197 51 597 A1 9/1999
DE 696 30 181 T2 8/2004
(Continued)

OTHER PUBLICATIONS

"Modes of Ventilation in Intensive Care," Karin Deden, Dräger Medical GmbH.
(Continued)

*Primary Examiner* — Joseph D. Boecker
(74) *Attorney, Agent, or Firm* — McGlew and Tuttle, P.C.

(57) ABSTRACT

An anesthesia ventilator, for the automated ventilation of a patient, includes an expiratory port and an inspiratory port for connecting a ventilation tube facing the patient for a breathing gas, a breathing gas delivery unit, at least one breathing gas sensor for detecting an anesthetic gas concentration, at least one pressure sensor for detecting a pressure of the breathing gas, as well as at least one computer. The computer is configured to actuate the breathing gas delivery unit as a function of the detected pressure of a preset desired
(Continued)

pressure value. The computer is further configured to perform an adaptation of the desired pressure value as a function of the detected anesthetic gas concentration.

18 Claims, 13 Drawing Sheets

(51) Int. Cl.
| | |
|---|---|
| *A61M 16/20* | (2006.01) |
| *A61M 16/08* | (2006.01) |
| *A61M 16/10* | (2006.01) |
| *A61B 5/08* | (2006.01) |
| *A61B 5/00* | (2006.01) |
| *G16H 40/60* | (2018.01) |
| *G16H 20/40* | (2018.01) |
| *A61M 16/22* | (2006.01) |

(52) U.S. Cl.
CPC .... *A61M 16/0003* (2014.02); *A61M 16/0051* (2013.01); *A61M 16/01* (2013.01); *A61M 16/085* (2014.02); *A61M 16/0833* (2014.02); *A61M 16/0858* (2014.02); *A61M 16/0891* (2014.02); *A61M 16/104* (2013.01); *A61M 16/208* (2013.01); *G16H 20/40* (2018.01); *G16H 40/60* (2018.01); *A61M 16/0072* (2013.01); *A61M 16/22* (2013.01); *A61M 2016/0027* (2013.01); *A61M 2016/0036* (2013.01); *A61M 2016/0039* (2013.01); *A61M 2205/50* (2013.01); *A61M 2230/43* (2013.01); *A61M 2230/432* (2013.01); *A61M 2230/437* (2013.01); *A61M 2230/46* (2013.01)

(58) Field of Classification Search
CPC ............ A61M 16/085; A61M 16/0858; A61M 16/0891; A61M 16/104; A61M 16/22; A61M 2016/0027; A61M 2016/103; A61M 2016/1035; A61M 2230/005; A61M 2230/432; A61M 2230/437; A61B 5/082; A61B 5/4821
See application file for complete search history.

(56) References Cited

U.S. PATENT DOCUMENTS

| | | | |
|---|---|---|---|
| 6,131,571 A | 10/2000 | Lampotang et al. | |
| 2008/0283059 A1* | 11/2008 | Siegel | A61M 16/0093 128/203.25 |
| 2009/0293872 A1* | 12/2009 | Bocke | A61M 16/0093 128/203.14 |
| 2011/0000488 A1* | 1/2011 | Blomberg | A61M 16/01 128/203.14 |
| 2012/0031402 A1* | 2/2012 | Loncar | A61M 16/0093 128/203.14 |
| 2014/0352693 A1* | 12/2014 | Pessala | A61M 16/18 128/203.14 |
| 2018/0353717 A1* | 12/2018 | Buschke | A61M 16/0003 |

FOREIGN PATENT DOCUMENTS

| | | | |
|---|---|---|---|
| DE | 10 2011 10 6406 A1 | 1/2013 | |
| EP | 2572748 A1 * | 3/2013 | ............ A61M 16/18 |
| EP | 25 72 748 B1 | 5/2014 | |

OTHER PUBLICATIONS

"Zeus Infinity Empowered" Manual, Dräger Medical AG & Co. KG, 1st edition, Feb. 2009.
Primus Infinity Empowered, Dräger Medical GmbH, Edition Mar. 9, 2010 on pp. 132-134.

* cited by examiner

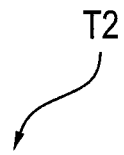

| | Level of ventilation | | |
|---|---|---|---|
| normal ventilated | Lung mechanic | | |
| KOZ Parameter | normal | obstructive | restrictive |
| etCO$_2$U1 [mmHg] | 45 | 55 | 45 |
| etCO$_2$O1 [mmHg] | 55 | 65 | 55 |
| | Level of ventilation | | |
| mild hyperventilated | Lung mechanic | | |
| KOZ Parameter | normal | obstructive | restrictive |
| etCO$_2$U1 [mmHg] | n/a | n/a | n/a |
| etCO$_2$O1 [mmHg] | n/a | n/a | n/a |
| | Lung mechanic | | |
| KOZ Parameter | normal | obstructive | restrictive |
| VTU1 [ml/kg] | 4 | 4 | 2 |
| VTO1 [ml/kg] | 6 | 6 | 4 |

FIG. 9

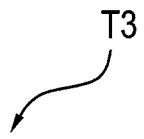

| Classification of Ventilation ($V_T$) (CoV_VT) | |
|---|---|
| $V_T$ | $V_T$-Range |
| very low | VT < VTU2 |
| low | VTU2 < VT < VTU1 |
| normal | VTU1 ≤ VT ≤ VTO1 |
| high | VTO2 > VT > VTO1 |
| very high | VT > VTO2 |

| Classification of Ventilation $etCO_2$ (CoV_$etCO_2$) | |
|---|---|
| $etCO_2$ | $etCO_2$.Range |
| severe hyperventilated | $etCO_2$ < $etCO_2$U2 |
| mild hyperventilated | $etCO_2$U2 < $etCO_2$ < $etCO_2$U1 |
| normoventilated | $etCO_2$U1 ≤ $etCO_2$ ≤ $etCO_2$O1 |
| mild hypoventilated | $etCO_2$O2 > $etCO_2$ > $etCO_2$O1 |
| severe hypoventilated | $etCO_2$ > $etCO_2$O2 |

| Check etCO2 | Check VT | dP | dRR |
|---|---|---|---|
| normo | very low | + 2 mbar | - 2 bpm |
| normo | low | + 1 mbar | - 1 bpm |
| normo | normal | • | • |
| normo | high | - 1 mbar | + 1 bpm |
| normo | very high | - 2 mbar | + 2 bpm |
| mild hyper | very low | • | - 1 bpm |
| mild hyper | low | • | - 1 bpm |
| mild hyper | normal | • | - 1 bpm |
| mild hyper | high | - 1 mbar | • |
| mild hyper | very high | - 2 mbar | • |
| severe hyper | very low | • | - 2 bpm |
| severe hyper | low | • | - 2 bpm |
| severe hyper | normal | • | - 2 bpm |
| severe hyper | high | - 1 mbar | - 1 bpm |
| severe hyper | very high | - 2 mbar | - 1 bpm |
| mild hypo | very low | + 2 mbar | • |
| mild hypo | low | + 1 mbar | • |
| mild hypo | normal | • | + 1 bpm |
| mild hypo | high | • | + 1 bpm |
| mild hypo | very high | • | + 1 bpm |
| severe hypo | very low | + 2 mbar | + 1 bpm |
| severe hypo | low | + 1 mbar | + 1 bpm |
| severe hypo | normal | • | + 2 bpm |
| severe hypo | high | • | + 2 bpm |
| severe hypo | very high | • | + 2 bpm |

T6

| | End Criteria | | |
|---|---|---|---|
| | Lung mechanic | | |
| Parameter | normal | obstructive | restrictive |
| etCO2G [mmHg] | < 50 | < 60 | < 50 |
| VTG [ml/kg] | > 3 | > 4 | >3 |
| RRsponG [bpm] | ≥ 8 | ≥ 8 | ≥ 8 |
| $\Delta$PG [mbar] | ≤ 7 | ≤ 7 | ≤ 7 |

FIG. 13

ANESTHESIA VENTILATOR FOR THE AUTOMATED VENTILATION OF A PATIENT

CROSS REFERENCE TO RELATED APPLICATIONS

This application is a United States National Phase Application of International Application PCT/EP2016/001952, filed Nov. 21, 2016, and claims the benefit of priority under 35 U.S.C. § 119 of German Application 10 2015 015 440.0, filed Dec. 2, 2015, the entire contents of which are incorporated herein by reference.

FIELD OF THE INVENTION

The present invention relates to anesthesia ventilators (also known as respirators) for the automated ventilation of a patient and also relates to a process for operating an anesthesia ventilator for the automated ventilation of a patient.

BACKGROUND OF THE INVENTION

Anesthesia ventilators as well as processes in which ventilation is carried out in an automated manner as a function of a desired pressure value as well as of a pressure of a breathing gas, which pressure is detected by a pressure sensor, are known from the state of the art.

Further, processes are known in which a so-called weaning is carried out, during which the patient is maintained in a so-called comfort zone, wherein a desired pressure value or a pressure support value is adapted as a function of a detected tidal volume as well as of an end-expiratory carbon dioxide concentration value for the purpose of weaning within the framework of a pressure support ventilation. Such processes are also known as so-called "Smart-Care/PS" processes.

SUMMARY OF THE INVENTION

An object of the present invention is to carry out an anesthesia ventilation of a patient in an automated manner, wherein a preset desired pressure value is taken into consideration for the ventilation and wherein the ventilation is carried out such that the ventilation of the patient is adapted in an advantageous manner.

According to the invention, an anesthesia ventilator is provided for the automated ventilation of a patient. The anesthesia ventilator comprises an expiratory port and an inspiratory port for connecting a ventilation tube facing the patient for a breathing gas, a breathing gas delivery unit, at least one breathing gas sensor for detecting an anesthetic gas concentration, at least one pressure sensor for detecting a pressure of the breathing gas, as well as at least one computer. The computer is configured to actuate the breathing gas delivery unit as a function of the detected pressure and of a preset desired pressure value and wherein the computer is further configured to perform an adaptation of the desired pressure value as a function of the detected gas concentration. The anesthesia ventilator according to the invention is advantageous because the ventilation of the patient can be adapted to the current anesthesia situation based on the adaptation of the desired pressure value as a function of the detected anesthetic gas concentration.

The computer is preferably configured to determine a mean alveolar anesthetic gas concentration as well as an end-expiratory anesthetic gas concentration on the basis of the detected anesthetic gas concentration, and further to perform an adaptation of the desired pressure value as a function of the determined mean alveolar anesthetic gas concentration as well as as a function of the determined end-expiratory anesthetic gas concentration. This embodiment of the present invention is advantageous because not only a mean alveolar anesthetic gas concentration is taken into consideration as an indication of the presence, in general, of anesthetic gas in the breathing gas, but an anesthetic gas concentration during the end-expiratory phase, which provides information as to the degree at which the patient breaks down the anesthetic by means of his metabolism, is taken into consideration as well. Thus, by taking into consideration these two variables concerning the anesthetic, the desired pressure value can be adapted more accurately. It is possible, for example, that even though the mean alveolar anesthetic gas concentration decreases over time, the anesthetic gas concentration does not continue to decrease as desired because of an insufficient metabolism of the anesthetic by the patient, so that the ventilation of the patient can be adapted to this by adapting the desired pressure value as a function of the two concentrations.

Further, the device preferably has at least one volume flow sensor for detecting a volume flow of the breathing gas and further at least one breathing gas sensor for detecting a carbon dioxide concentration in the breathing gas, and the computer is further configured to perform an adaptation of the desired pressure value as well as of a minimum ventilation rate as a function of the detected volume flow and as a function of the detected carbon dioxide concentration. This embodiment of the present invention is advantageous because the desired pressure value and the minimum ventilation rate can be adapted even more accurately, because not only an anesthetic gas concentration is taken into consideration for this, but the carbon dioxide concentration in the breathing gas as well as the volume, which indicates a tidal volume of the patient, is taken into consideration as well.

The computer is preferably configured to determine a tidal volume fed to the patient on the basis of the detected volume flow and further to determine an end-expiratory carbon dioxide concentration on the basis of the detected carbon dioxide concentration, and the computer is further configured to perform the adaptation of the desired pressure value as a function of the determined tidal volume, of an upper volume limit value, of a lower volume limit value, of the determined end-expiratory carbon dioxide concentration, of an upper concentration limit value and of a lower carbon dioxide limit value. This embodiment of the present invention is advantageous because a so-called comfort zone is defined by the respective limit values relative to the tidal volume and relative to the end-expiratory carbon dioxide concentration, and the adaptation of the ventilation rate and of the desired pressure value is performed by a comparison of the limit values of this comfort zone and of the tidal volume, on the one hand, as well as of the end-expiratory carbon dioxide concentration, on the other hand, in order thus to possibly maintain the patient within this comfort zone during the ventilation or to move him towards the comfort zone.

The computer is preferably configured to detect a desired operating state concerning the automated ventilation as a function of the determined tidal volume, of the determined end-expiratory carbon dioxide concentration, of another preset volume limit value, of another preset concentration limit value, of the current desired pressure value as well as of a preset desired pressure limit value, and to output an output signal, which indicates the presence of the desired operating state, for a clinician in case of detection. Such an operating state is given if the tidal volume and the end-expiratory carbon dioxide concentration have respective desired correlations with the respective limit values. If the operating state is present, this can be an indication for a clinician that the patient possibly has a desired respiratory characteristic. The outputting of the output signal, which indicates the presence of the operating state of the device concerning the automated ventilation, can be an indication for a clinician to take extubation of the patient into consideration. Such a situation is present, for example, when the supply of anesthetic gas through the anesthetic gas-mixing unit within the ventilator was interrupted before by the clinician and the clinician would then like to possibly take an extubation into consideration during the end phase of the anesthesia ventilation.

The computer is preferably configured to actuate the breathing gas delivery unit such that the automated ventilation is carried out as a pressure support ventilation. This embodiment of the present invention is advantageous because a pressure support ventilation requires a spontaneous breathing activity of a patient, which is desirable especially during end phases of an anesthetic ventilation.

Further, the device preferably has at least one volume flow sensor for detecting a volume flow of the breathing gas, wherein the computer is further configured to detect an attempt at spontaneous breathing by the patient and further to carry out the pressure support ventilation with the use of the desired pressure value when a spontaneous attempt at breathing is detected. This embodiment of the present invention is advantageous because a spontaneous breathing activity of a patient can be detected hereby.

The computer is further preferably configured to control the output of a warning signal as a function of detected attempts at spontaneous breathing and as a function of a presettable minimum ventilation rate. This embodiment of the present invention is advantageous because if the ventilation is possibly too low based on the patient's own spontaneous breathing activity, i.e., if a minimum respiration rate is fallen below, the clinician is informed that he could possibly take actions himself to change the patient's current ventilation situation.

According to a further aspect of the invention, a process is provided for operating an anesthesia ventilator for the automated ventilation of a patient, comprising the steps of: feeding of a breathing gas to a patient via an inspiratory port and return of the breathing gas via an expiratory port by operating a breathing gas delivery unit, detection of an anesthetic gas concentration by means of at least one breathing gas sensor, detection of a pressure of the breathing gas by means of at least one pressure sensor, and actuation of the breathing gas delivery unit as a function of the detected pressure and of a preset desired pressure value by means of at least one computer, characterized by the adaptation of the desired pressure value as a function of the detected anesthetic gas concentration by means of the computer.

Further, a computer for an anesthesia ventilator for the automated ventilation of a patient is provided, which is configured to detect an anesthetic gas concentration signal, which indicates an anesthetic gas concentration in a breathing gas, to detect a pressure signal, which indicates a pressure of the breathing gas, and to provide an actuating signal for a breathing gas delivery unit, wherein the computer determines the actuating signal as a function of the detected pressure signal and of a preset desired pressure value and wherein the computer is further configured to perform an adaptation of the desired pressure value as a function of the detected anesthetic gas concentration signal.

Further, a process for operating an anesthesia ventilator for the automated ventilation of a patient is provided, which has the steps: detection of an anesthetic gas concentration signal, which indicates an anesthetic gas concentration in a breathing gas, detection of a pressure signal, which indicates a pressure of the breathing gas, provision of an actuating signal for a breathing gas delivery unit as a function of the detected pressure signal and of a preset desired pressure value, characterized by the adaptation of the desired pressure value as a function of the detected anesthetic gas concentration signal.

Further, the above-mentioned process for operating an anesthesia ventilator for the automated ventilation of a patient is provided, wherein the process is carried out with a computer program on at least one computer.

Advantages of the anesthetic gas ventilator being proposed also apply to the process proposed for the automated ventilation of a patient. These advantages likewise apply to the computer being proposed for an anesthesia ventilator. These advantages likewise apply to a process for operating an anesthesia ventilator as well.

The present invention will be explained in more detail below on the basis of special embodiments without limitation of the general inventive idea on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 9 is a table of possible limit values for carrying out the process according to the present invention;

FIG. 10 is a view of tables for determining degrees of ventilation and gas exchange rates relative to a tidal volume and an end-expiratory carbon dioxide concentration;

FIG. 11 is a table of values for the adaptation of the desired pressure value and for the adaptation of the minimum ventilation rate;

FIG. 13 is a table showing limit values for the detection of an operating state concerning the automated ventilation.

DESCRIPTION OF THE PREFERRED EMBODIMENTS

Figure 1:
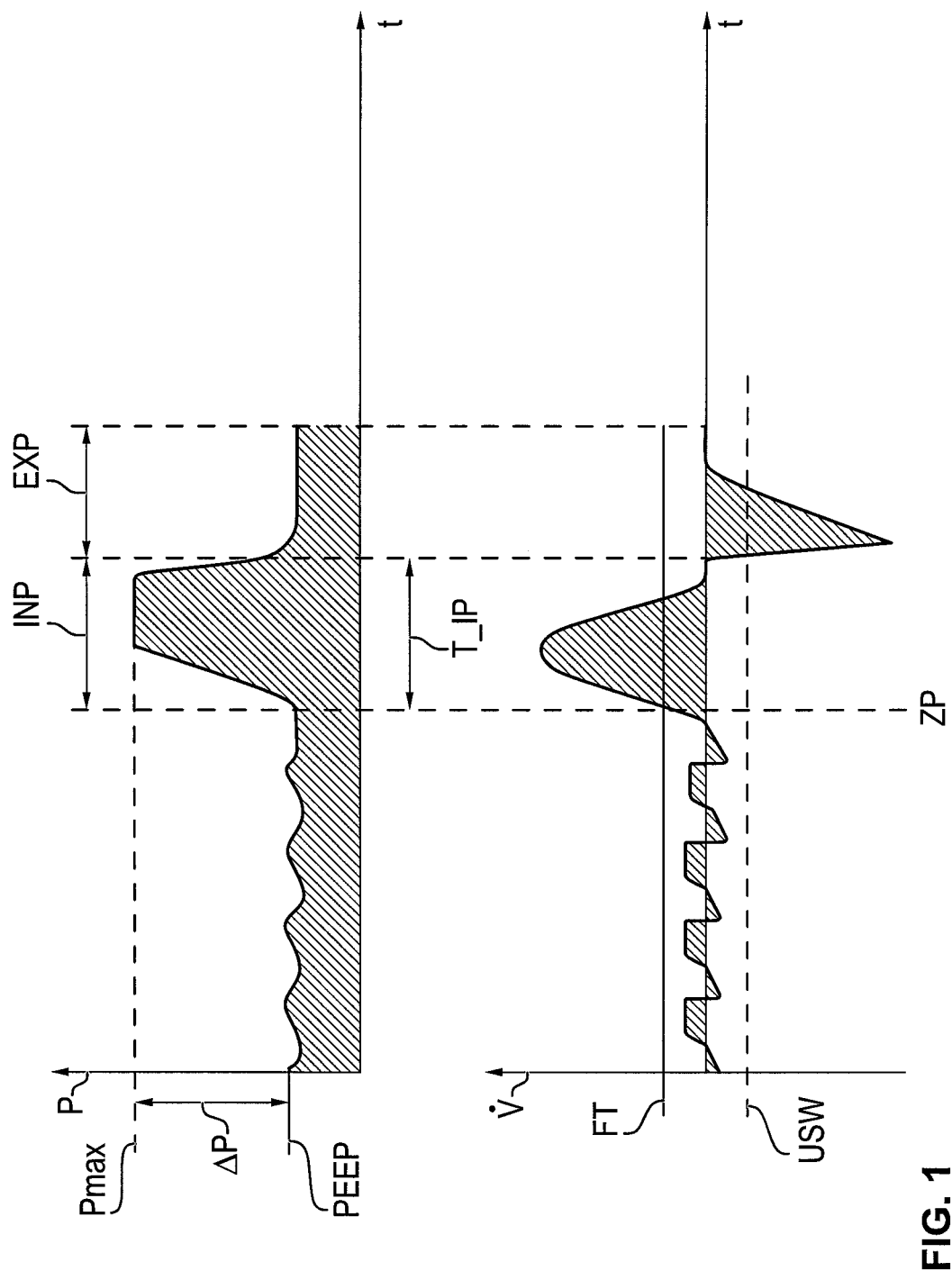
FIG. 1 is a graph view showing a pressure curve over time as well as a volume flow curve over time in the course of an inhalation and an exhalation.
Figure 2:
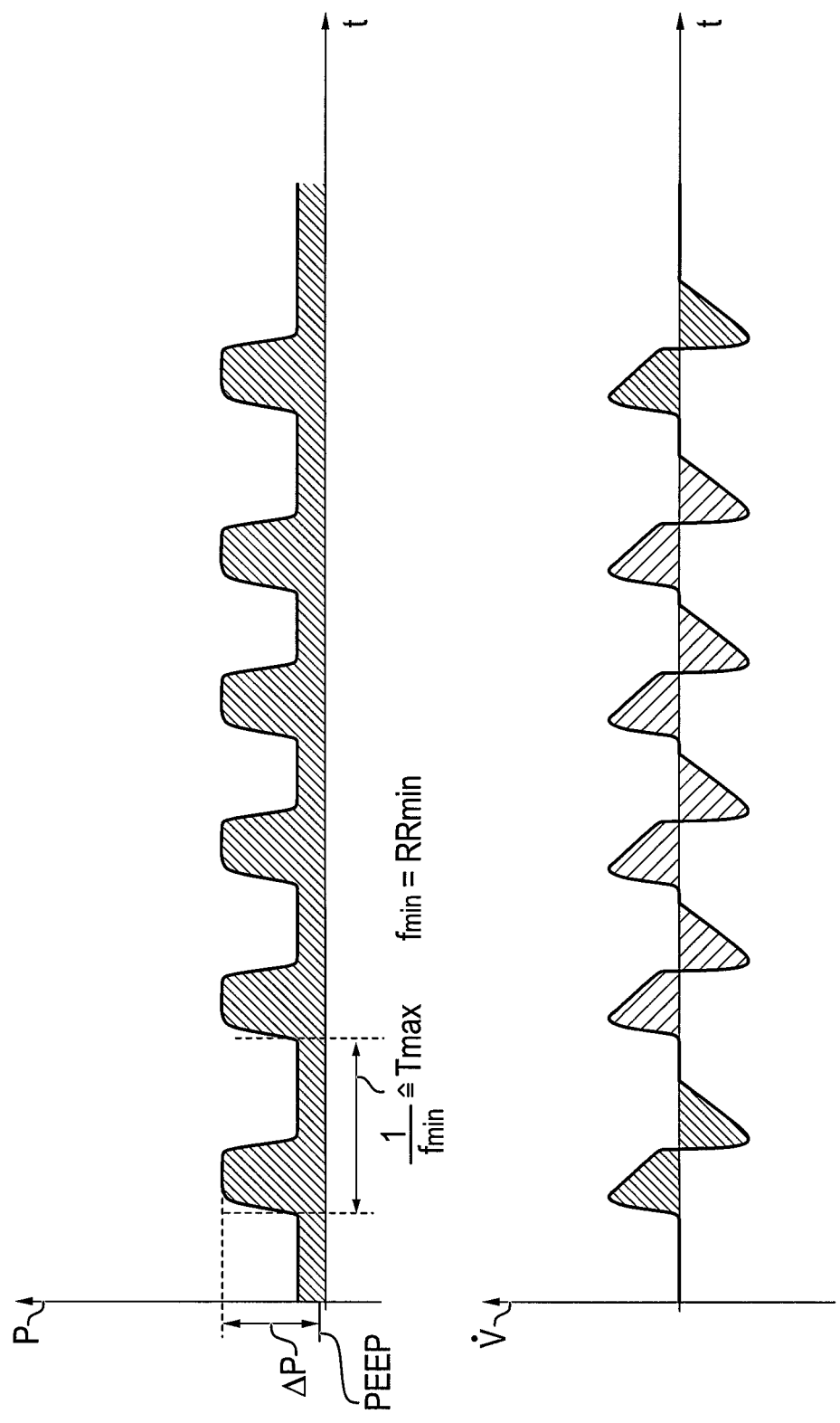
FIG. 2 is a graph view showing a pressure curve over time as well as a volume flow curve over time within the framework of a pressure support ventilation, during which attempts at spontaneous breathing by a patient are made possible.

Referring to the drawings, FIGS. 1 and 2 show curves known from the state of the art, on the basis of which the principles of a trigger control in the course of a pressure support ventilation will now be explained in more detail. These principles can also be found in the documents:

"Modes of Ventilation in Intensive Care," Karin Deden, Dräger Medical GmbH; as well as "Zeus Infinity Empowered" Manual, Dräger Medical AG & Co. KG, 1st edition, February 2009.

FIG. 1 shows for the illustration of a trigger control a pressure curve of a pressure value P over time, and it further shows a curve of a volume flow $\dot{V}$ over time. If a patient is ventilated by an anesthesia ventilator, a pressure support takes place such that the pressure is maintained at a minimum end-expiratory pressure PEEP (Positive End Expiratory Pressure) before an inspiratory phase INSP. If a patient makes an attempt at breathing spontaneously, this leads to the volume flow $\dot{V}$ to be exceeded above a so-called trigger threshold or flow trigger threshold FT at the time ZP. Then, when the threshold is exceeded, the pressure P is controlled such that the pressure P is controlled to a maximum Pmax, this maximum pressure Pmax being above the minimum pressure PEEP by a pressure difference ΔP. A duration T_IP is usually preset for an inspiratory phase, so that the end-expiratory phase EXP, during which the pressure P is again lowered to the minimum pressure PEEP, is started after the end of the duration T_IP. A negative volume flow $\dot{V}$ is thus obtained during the end-expiratory phase based on the flow of the volume flow $\dot{V}$ out of the patient.

Such a trigger-controlled ventilation is usually carried out within the framework of a pressure support ventilation, as it is shown once again in FIG. 2. Such a pressure support ventilation is preferably carried out, furthermore, such that the patient must bring about a minimum respiration rate fmin or RRmin based on his triggering, which is initiated by him, so that a maximum time window Tmax is obtained between two start times of contiguous inspiratory phases. If the breathing triggered by the patient causes no repeated inhalation to be carried out after the end of the time window Tmax, a warning may be outputted in such a case. Consequently, if the respiration rate of the spontaneous breathing of the patient is lower than the minimum ventilation rate fmin or RRmin, a warning, which indicates excessively weak spontaneous breathing of the patient, is outputted.

Figure 3:
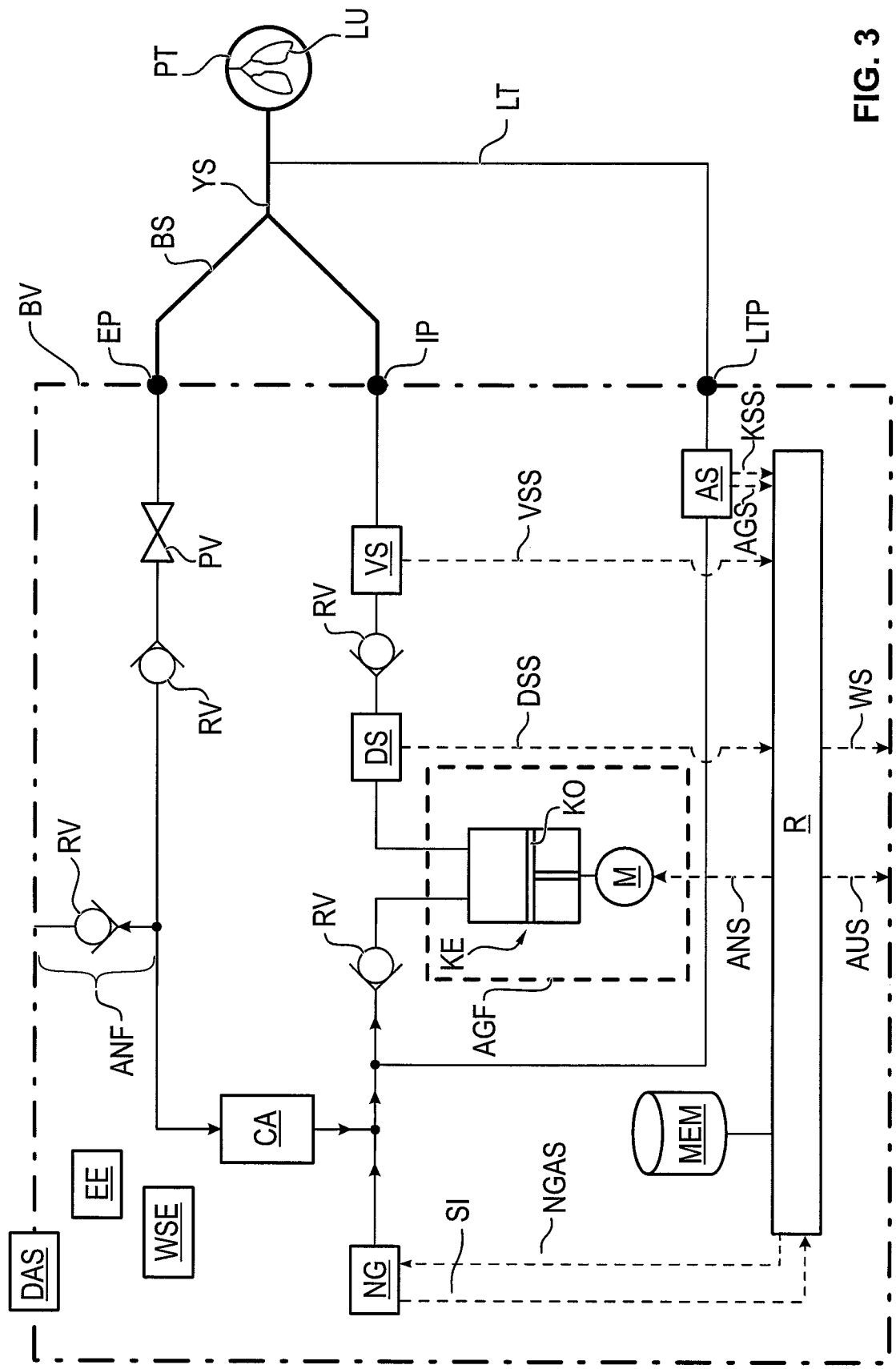
FIG. 3 is a schematic view showing an anesthetic ventilator according to the present invention.

FIG. 3 shows the device BV according to the present invention for the automated ventilation of a patient PT. The anesthesia ventilator BV according to the present invention has an inspiratory port IP and an expiratory port EP, to which a ventilation tube BS, which faces the patient PT, can be connected. A breathing gas is fed to the patient and is also removed from the patient to the device BV via this ventilation tube BS. The feeding is carried out via the inspiratory port IP, and the removal takes place via the expiratory port EP. The ventilation tube BS merges the connections of the ports EP, IP at a so-called Y-piece YS, which then usually ends at a tube, which is inserted into the patient PT in order to ventilate his lungs LU.

The anesthesia ventilator BV further has a breathing gas delivery unit AGF. The breathing gas delivery unit AGF is preferably a piston unit KE, in which a piston KO can be moved to and fro by a motor M.

The device BV has at least one computer R. The computer R is at least one computer, which may also be embodied by a network of a plurality of computers.

The anesthesia ventilator BV further has a pressure sensor DS for detecting a pressure of the breathing gas. The pressure sensor DS provides a pressure sensor signal DSS to the computer R.

A minimum pressure PEEP is preferably generated by a valve PV, which is preferably located in the area of the expiratory port EP.

The anesthesia ventilator BV further has a breathing gas sensor AS. The breathing gas sensor AS is configured to detect an anesthetic gas concentration in the breathing gas. The breathing gas sensor AS provides an anesthetic gas concentration signal AGS to the computer R. Further, the breathing gas sensor AS is preferably configured to detect a carbon dioxide concentration in the breathing gas. The breathing gas sensor AS preferably provides a carbon dioxide concentration signal KSS to the computer R. The breathing gas sensor AS is preferably not an individual sensor but a sensor unit, which has a plurality of sensors, each having a special configuration, for detecting the respective aforementioned concentrations.

The sensor AS is preferably provided behind a measuring line LT, which removes a measuring sample of the breathing gas at the Y-piece YS and is connected to a measured gas port LTP.

The anesthesia ventilator BV has a carbon dioxide absorber CA as well as an anesthetic gas-mixing unit NG. A gas mixture necessary for the anesthesia can then be introduced into the closed breathing circuit via the anesthetic gas-mixing unit NG. Such a gas mixture thus contains at least one anesthetic.

The anesthetic ventilator further has an anesthetic gas discharge line ANF or a connection to an anesthetic gas discharge line ANF. The gas flow within the anesthesia ventilator BV is preferably controlled by nonreturn valves RV. The computer R controls the anesthetic gas-mixing unit NG by means of a control signal NGAS. The anesthetic gas-mixing unit NG preferably provides for the computer R a status signal SI, which indicates whether or not the anesthetic gas-mixing unit NG is introducing an anesthetic into the breathing gas. This status signal preferably indicates whether an anesthetic evaporator is opened or not.

The anesthesia ventilator BV preferably has at least one volume flow sensor VS for detecting a volume flow of the breathing gas. The volume flow sensor VS provides a volume flow signal VSS to the computer R.

Figure 5:
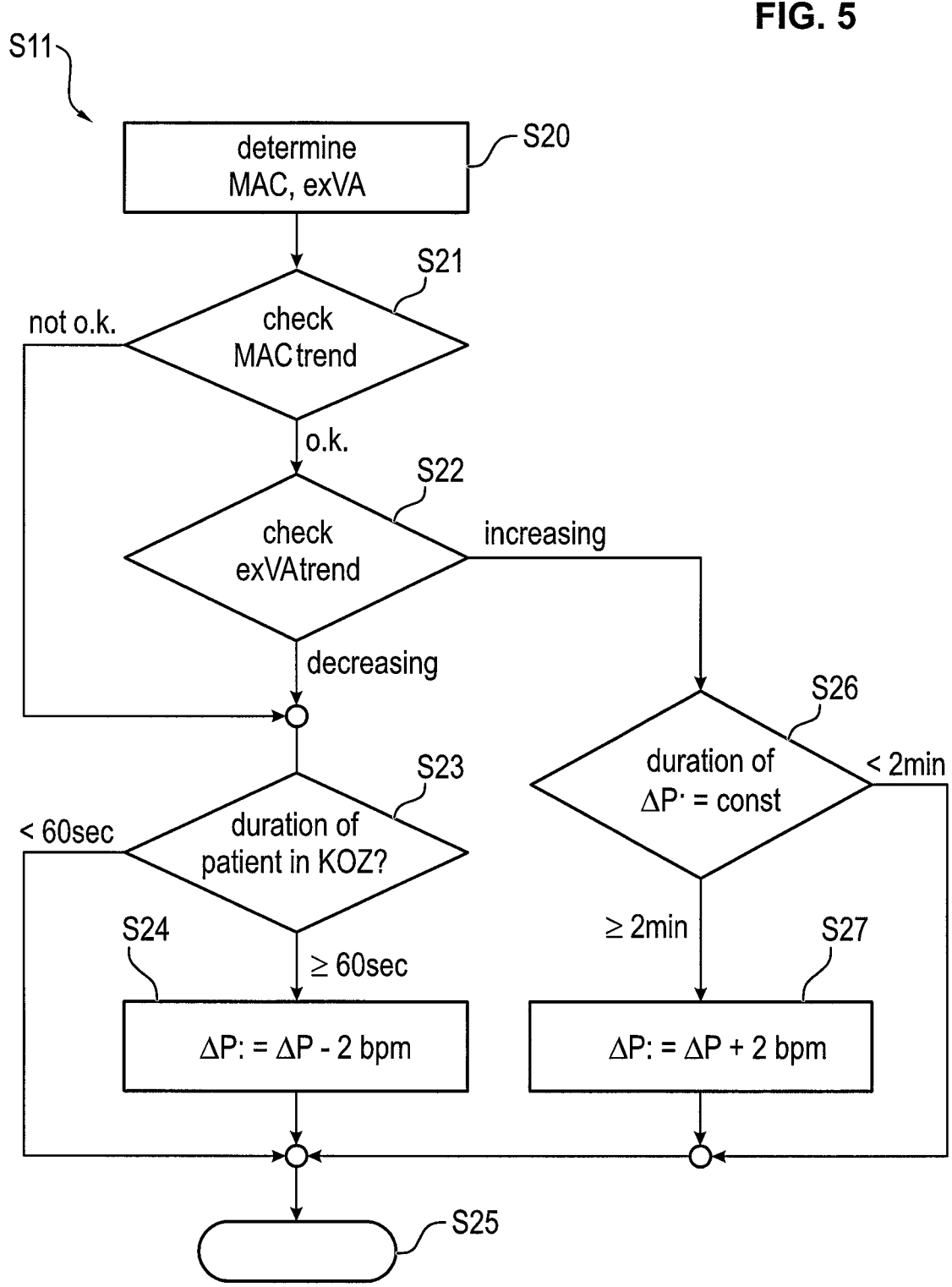
FIG. 5 is a flow diagram showing first partial steps of the process according to the present invention.

The anesthesia ventilator BV from FIG. 5 preferably has an input unit EE or an interface EE for an input unit, by means of which inputs, which may be made by an operator or clinician at the input unit, can be received at the anesthesia ventilator BV.

The computer R preferably accesses a memory unit MEM in order to carry out the process according to the present invention.

The computer R preferably outputs a warning signal WS in the above-described manner in order to indicate the presence of a ventilation rate that is below the minimum ventilation rate. This output is preferably effected via a data interface DAS of the device BV. The device BV itself preferably has a warning signal output unit WSE, which may preferably output an optical and/or acoustic warning.

Figure 4:
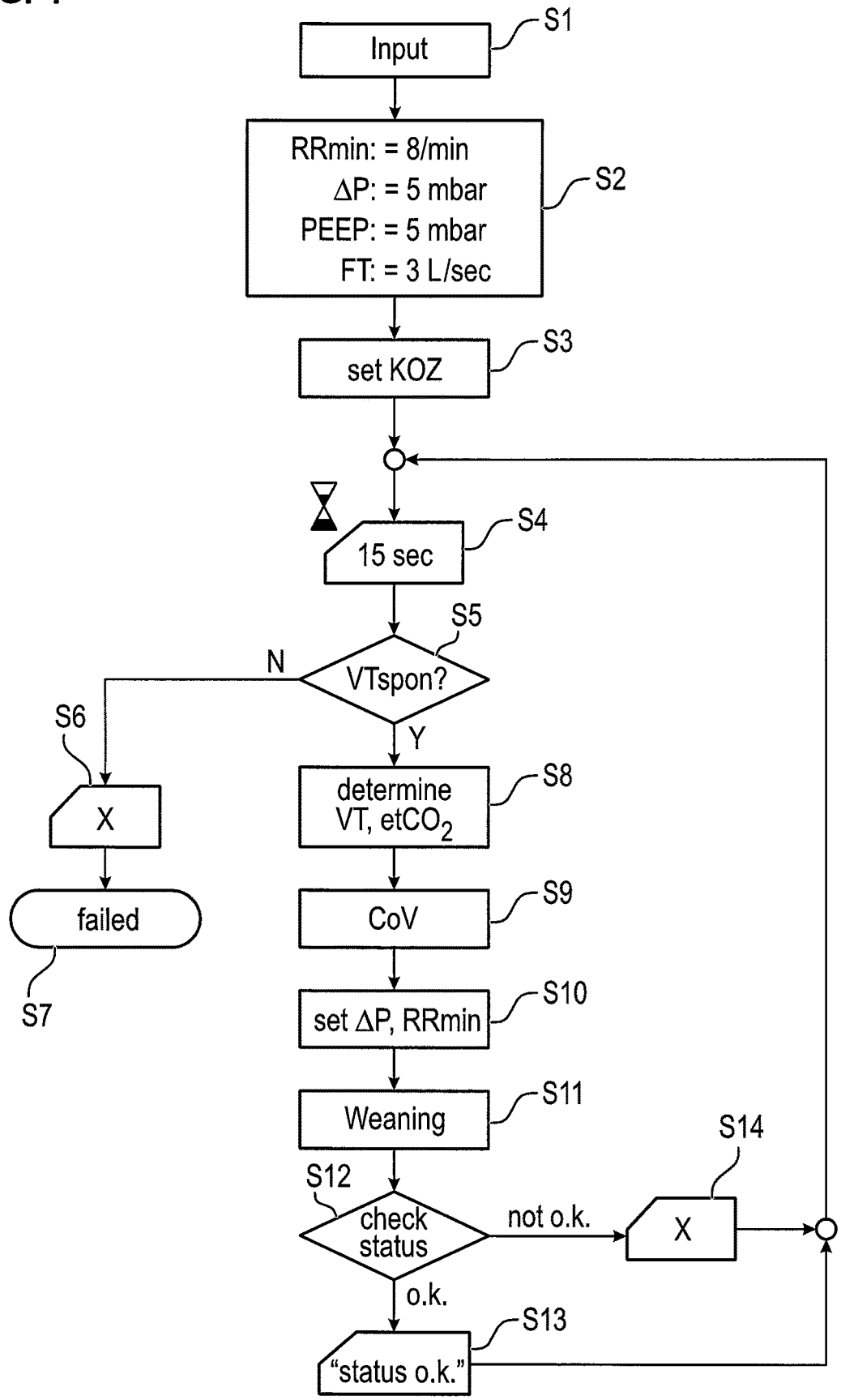
FIG. 4 is a flow diagram showing steps of the process according to the present invention.

The anesthesia ventilator according to the present invention is preferably configured to carry out a pressure support ventilation of the patient PT. FIG. 4 shows steps by means of which the anesthesia ventilator from FIG. 3 can be prompted to carry out the process according to the present invention.

Figure 8:
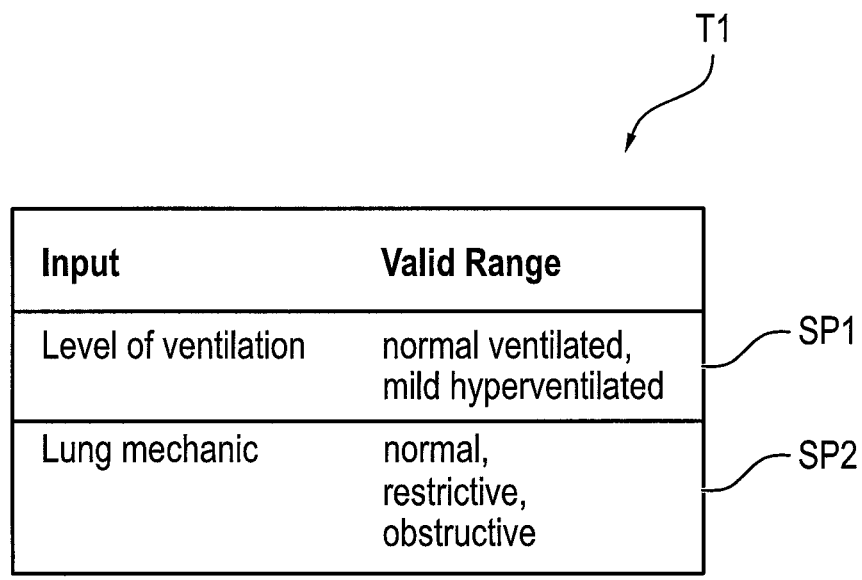
FIG. 8 is a table of preset values presettable by a clinician.

In Table T1, FIG. 8 shows possibilities of various inputs, which can be inputted by a clinician within the framework of step S1 of FIG. 4. The first column SP1 contains different entries or specifications, by means of which a desired degree of ventilation or a desired gas exchange rate of a patient can be selected. These are preferably the variants of a normal ventilation or of a mild hyperventilation. Such inputs can be received by the interface EE shown in FIG. 3 or the input unit EE of the anesthesia ventilator BV. This input unit EE may preferably be an input unit belonging to the anesthesia ventilator BV or an input unit communicating with the anesthesia ventilator BV in the form of a keyboard, a touchscreen and/or a computer mouse.

The second column SP2 of FIG. 8 contains, further, different possibilities of specifications concerning a lung property ("Lung Mechanic") of the patient. The specification may indicate a lung property of normal, restrictive or obstructive lungs of a patient.

Coming back to FIG. 4, an initialization of ventilation-relevant parameters may now be performed in step S2. The minimum ventilation rate RRmin is preferably set at 8 breaths per minute, the pressure difference ΔP at 5 mbar, the minimum pressure PEEP at 5 mbar and the trigger threshold FT at 3 L/sec. It is clear to a person skilled in the art and he can see that the values being shown here are only exemplary values and they may also be selected differently when carrying out the process according to the present invention as well as when embodying the device according to the present invention.

Figure 7:
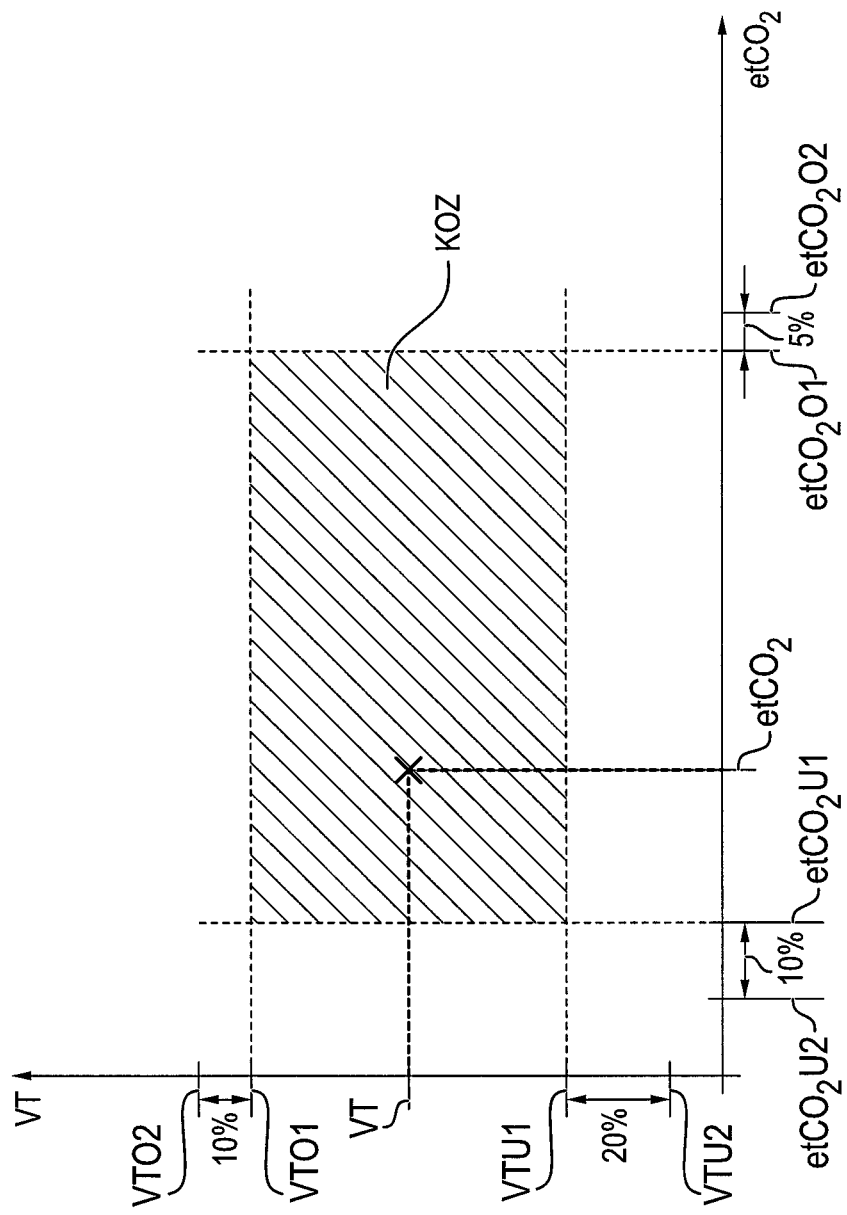
FIG. 7 is a graph view showing an illustration of limit values.

Different limit values, which may be considered to be a so-called comfort zone KOZ, are preferably initialized in a step S3. FIG. 7 may be examined for this in connection with this step S3.

FIG. 7 indicates the comfort zone KOZ, which is present whenever a tidal volume VT inhaled by the patient, which is between an upper volume limit value VTO1 and a lower volume limit value VTU1, is determined by the computer from a detected volume flow. It is further necessary for attaining the comfort zone KOZ that an end-expiratory carbon dioxide concentration etCO2, determined by the computer R on the basis of the carbon dioxide concentration signal KSS, which is between an upper concentration limit value etCO2O1 and a lower concentration limit value etCO2U1, be present.

An object of the process that is preferably to be achieved is to ventilate the patient such that the patient has or breathes a tidal volume VT that is within the volume limit values VTO1, VTU1 due to the ventilation and that the patient also has at the same time an end-expiratory carbon dioxide concentration etCO2 that is within the concentration limit values etCO2U1 and etCO2O1.

In reference to step S3 from FIG. 4, it can be determined from an additional examination of FIG. 9 and by examining Table T2 how the respective volume limit values VTO1, VTU1 as well as the respective concentration limit values etCO2U1, etCO2O1 can be selected by selecting the specifications concerning the lung property of the patient as well as the gas exchange rate or the degree of ventilation. No provisions are explicitly made in this connection in this exemplary embodiment for the degree of ventilation "mildly hyperventilated" to be able to be selected by a previous input by the clinician, as is indicated by the entries "n/a." As an alternative, it is, however, possible to provide values instead of the entries "n/a," so that corresponding limit values of the carbon dioxide concentration etCO2U1, etCO2O1 can then be selected when selecting the degree of ventilation "mildly hyperventilated."

The computer R of FIG. 3 preferably determines a tidal volume inhaled by the patient on the basis of the detected volume flow. The computer preferably determines for this the tidal volume as an integral value of the volume flow over this duration T_IP on the basis of the detected volume flow and of a preset duration T_IP. As an alternative, a duration of an inspiratory phase may be determined by inferring a beginning of the inspiratory phase when a volume flow threshold value is exceeded and an end of the inspiratory phase when the volume flow threshold value is fallen below.

The computer preferably determines an end-expiratory carbon dioxide concentration on the basis of the detected carbon dioxide concentration. The end of an expiratory phase is then inferred preferably by a comparison of the volume flow, as is shown in FIG. 1, and of a lower or negative USW threshold value when the detected volume flow passes through the lower threshold value USW from below.

The values determined by the computer R of FIG. 3 for the tidal volume as well as the end-expiratory carbon dioxide concentration are preferably provided as measured values every 4 sec.

According to step S4 of FIG. 4, there is at first a waiting period of 15 sec, and the tidal volume VT taken into consideration is then preferably determined, within the framework of step S8, by means of a median filtering of the measured values of the tidal volume that were present in the last 60 sec. The end-expiratory carbon dioxide concentration etCO2 taken into consideration is likewise preferably determined by means of a preprocessing, preferably a median filtering, on the basis of the measured values of the end-expiratory carbon dioxide concentration that represent the last 60 sec.

It will now be explained at first how an adaptation of the ventilation rate RRmin as well as a preferable adaptation of the desired pressure value ΔP are preferably carried out as a function of the tidal volume VT and as a function of the end-expiratory carbon dioxide concentration etCO2.

After determining the tidal volume VT as well as the end-expiratory carbon dioxide concentration etCO2 within the framework of step S8, a degree of ventilation is preferably determined first within the framework of step S9 with reference to the tidal volume and, further, a degree of ventilation is determined with reference to the end-expiratory carbon dioxide concentration. FIG. 10 is to be used for this, which presets different degrees of ventilation in Table T3 with a comparison of the total volume VT with the limit values determined previously. Not only the upper and lower limit values VTO1, VTU1, respectively, as they were shown before in Table T2, are used here, but preferably additional, second limit values VTO2, VTU2 as well. These second limit values VTO2, VTU2 are likewise shown in FIG. 7. Consequently, respective limit values VTO2, VTU2, in which a deviation by 10% or 20% from the first limit values VTO1, VTU1 is taken into consideration, are used.

A corresponding statement may also be made for the degree of ventilation in reference to the end-expiratory carbon dioxide concentration compared to the carbon dioxide values etCO2U1, etCO2O1 as well as additional, second concentration values etCO2U2, etCO2O2, which deviate from the first concentration values etCO2U1, etCO2O1 by 5% and 10%, respectively, and are likewise shown in FIG. 7. Consequently, a degree of ventilation can be determined with reference to the end-expiratory carbon dioxide concentration based on Table T4 of FIG. 10.

An adaptation of the desired pressure value ΔP as well as of the minimum ventilation rate is preferably carried out in step S10 shown in FIG. 4. This is carried out with the use of a Table T5 from FIG. 11.

Using the degrees of ventilation determined on the basis of Table T3 and Table T4 of FIG. 10 relative to the tidal volume VT and the end-expiratory carbon dioxide concentration etCO2, a change dP in the desired pressure value ΔP as well as a change dRR in the ventilation rate RRmin can now be determined on the basis of Table T5 of FIG. 11. Based on the determined changes dP as well as dRR, the desired pressure value ΔP as well as the ventilation rate RRmin are then adapted. This is carried out according to $$\Delta P := \Delta P + dP$$

$$RR\ min := RR\ min + dRR.$$

The ventilation rate RRmin is preferably used in the manner described before to detect whether the computer shall output a warning signal WS.

An adaptation of the desired pressure value ΔP is carried out according to the present invention in step S11 as a function of a detected anesthetic gas concentration. FIG. 5 shows partial steps of step S11 from FIG. 4 for this.

According to FIG. 5, a mean alveolar anesthetic gas concentration MAC is first determined in partial step S20. Such a mean alveolar anesthetic gas concentration is also called "Minimum Alveolar Concentration." This mean alveolar anesthetic gas concentration MAC is preferably a standardized variable xMAC or a MAC multiple, as is explained in more detail in the document: *Primus Infinity Empowered*, Dräger Medical GmbH, Edition Sep. 3, 2010 on pages 132-134.

Such a mean alveolar anesthetic gas concentration MAC is determined over an averaged time window of past measured values, which are indicated by the anesthetic gas concentration signal AGS, see FIG. 3.

Further, an end-expiratory anesthetic gas concentration exVA is determined. The computer R determines for this the concentration of the anesthetic gas on the basis of the anesthetic gas concentration signal AGS according to FIG. 3 preferably during an end-expiratory phase. The computer R can preferably detect for this the presence of an expiratory phase EXP from FIG. 1 with the use of the lower threshold value USW in the above-mentioned and above-described manner and take into account measured values of the anesthetic gas concentration that are measured during the end phase of the expiratory phase EXP.

A check is then performed in partial step S21 of FIG. 5 to determine whether a curve of the determined mean alveolar anesthetic gas concentration over time meets preset conditions over its course in time. If these conditions are not met, the process is branched off to a step S23. If these conditions are met, the process is branched off to a step S23, in which the end-expiratory carbon dioxide concentration is checked.

Figures 12A, 12B:
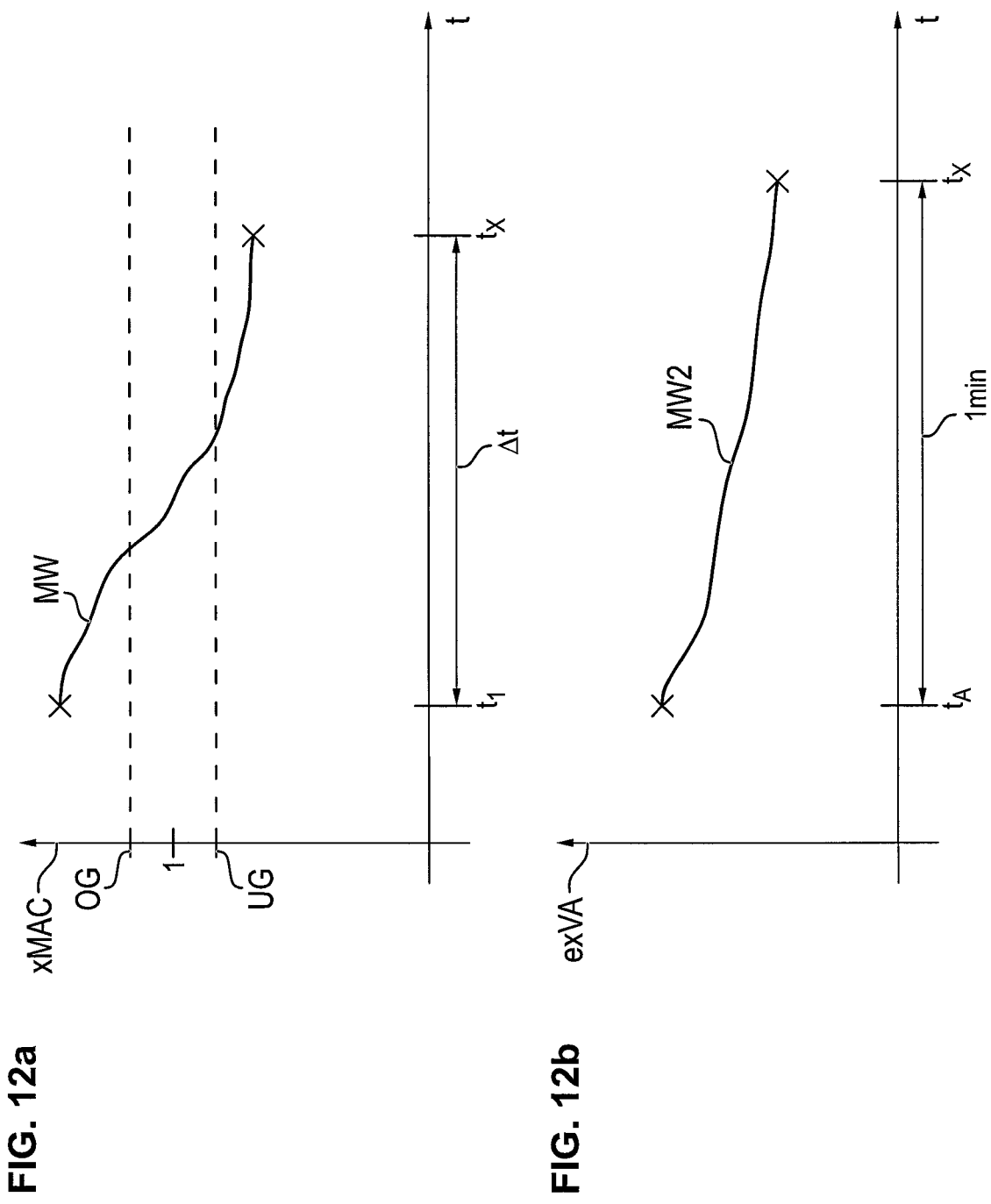
FIG. 12a is a graph view showing a curve of a mean alveolar anesthetic gas concentration over time.
FIG. 12b is a graph view showing a curve of an end-expiratory anesthetic gas concentration over time.

FIG. 12a illustrates a possible curve of the mean alveolar anesthetic gas concentration MAC over time for the step S21 of the checking. Measured values MW of the mean alveolar anesthetic gas concentration MAC are taken into consideration for a current time tX as well as for a time t1 preceding the first one by a preset time interval Δt. The mean alveolar anesthetic gas concentration MAC is preferably the aforementioned anesthetic gas concentration xMAC.

If, for the past time t1, the mean alveolar anesthetic gas concentration MAC is above an upper limit value OG, which is preferably the value "1.1" for xMAC, and if the mean alveolar anesthetic gas concentration MAC is below a lower limit value UG, which is preferably the value "0.9" for xMAC, an adequate reduction of the mean alveolar anesthetic gas concentration xMAC over time is assumed. The required conditions are therefore met in this case. The curve of the mean alveolar anesthetic gas concentration over time has a reduction over time, and it is to be expected and can be achieved during an end phase of an anesthetic ventilation. No more anesthetic gases are introduced into the breathing gas by the anesthetic gas-mixing unit NG according to FIG. 3 during such a phase.

Coming back to FIG. 5, it is then checked in partial step S22 whether a curve of the end-expiratory anesthetic gas concentration exVA over time is rising or falling. Partial step S22 of FIG. 5 will now be explained in more detail in connection with an examination of FIG. 12b.

FIG. 12b shows a possible time curve of measured values MW2 of the end-expiratory anesthetic gas concentration exVA over the time t. The respective measured values are taken into consideration for a current time tX as well as for a time tA preceding the current time by a preset period of preferably 1 minute. If a comparison of these measured values of the times tX, tA indicates a reduction of the end-expiratory anesthetic gas concentration, it is then inferred that the patient is breaking down or reducing the anesthetic still present in the breathing gas based on this metabolism. The process is therefore branched off in partial step S22 of FIG. 5 to partial step S23 of FIG. 5. If, however, contrary to what is shown in FIG. 12b, no reduction of the end-expiratory anesthetic gas concentration is determined, but an increase in the end-expiratory anesthetic gas concentration is detected, the process is branched off from partial step S22 to a partial step S26.

The period for which the parameters of the tidal volume as well as of the end-expiratory carbon dioxide concentration were present within the so-called comfort zone from FIG. 7 is detected in partial step S23. If this duration is longer than a preceding time period of 60 sec, the process is then preferably branched off to the partial step S24. If this duration is shorter than 60 sec, the process is preferably branched off to partial step S25, in which the partial process according to FIG. 5 ends. An adaptation of the desired pressure value ΔP is performed in partial step S24, preferably according to $$\Delta P := \Delta P - 2\ bpm.$$

If the process was branched off from partial step S22 to partial step S26, it is checked in partial step S26 how long the time period is for which the desired pressure value ΔP remained constant. If the desired pressure value ΔP remained constant for a preset time period of preferably 2 minutes, the process is branched off to partial process step S27, in which an adaptation of the desired pressure value ΔP is carried out, preferably according to $$\Delta P := \Delta P + 2\ bpm.$$

If the desired pressure value ΔP has not remained constant for the preset time period of preferably 2 minutes, the process is branched off directly to partial process step S25.

In summary, it can consequently be stated with reference to partial step S11 and FIG. 5 that a mean alveolar anesthetic gas concentration as well as an end-expiratory anesthetic gas concentration are determined on the basis of the anesthetic gas concentration, and an adaptation of the desired pressure value ΔP is performed as a function of the determined mean alveolar anesthetic gas concentration as well as as a function of the determined end-expiratory anesthetic gas concentration.

Further, the adaptation of the desired pressure value ΔP is carried out depending on whether the end-expiratory carbon dioxide concentration etCO2 and the tidal volume VT have met limit value conditions for a past time period of a preset duration, e.g., 60 sec. These are the limit value conditions that are defined by the first volume limit values and the first concentration limit values. These limit values define the comfort zone KOZ from FIG. 7.

Further, the adaptation of the desired pressure value ΔP is carried out as a function of whether the desired pressure value ΔP has remained constant for a second past time period, e.g., 2 minutes, when the process according to the present invention was carried out.

After reaching partial step S25 of FIG. 5, process step S11 from FIG. 4 is carried out to the end.

It is preferably detected in process step S12 of FIG. 4 whether a desired operating state is present concerning the automated ventilation. If yes, the process can then be continued to a process step S13, in which an output signal ("status OK"), which indicates the presence of the desired operating state, is outputted for a clinician. This output signal is the output signal AUS in FIG. 3, which is outputted by the computer R. This output signal AUS is preferably outputted by the computer R by means of a data interface DAS.

If the desired operating state was not detected, the process is branched off from process step S12 to a process step S14, in which an output signal, which was possibly outputted before, that from process step S13, is canceled. Process steps S13 and S14 continue the process, in which the process is then returned to process step S4.

Figure 6:
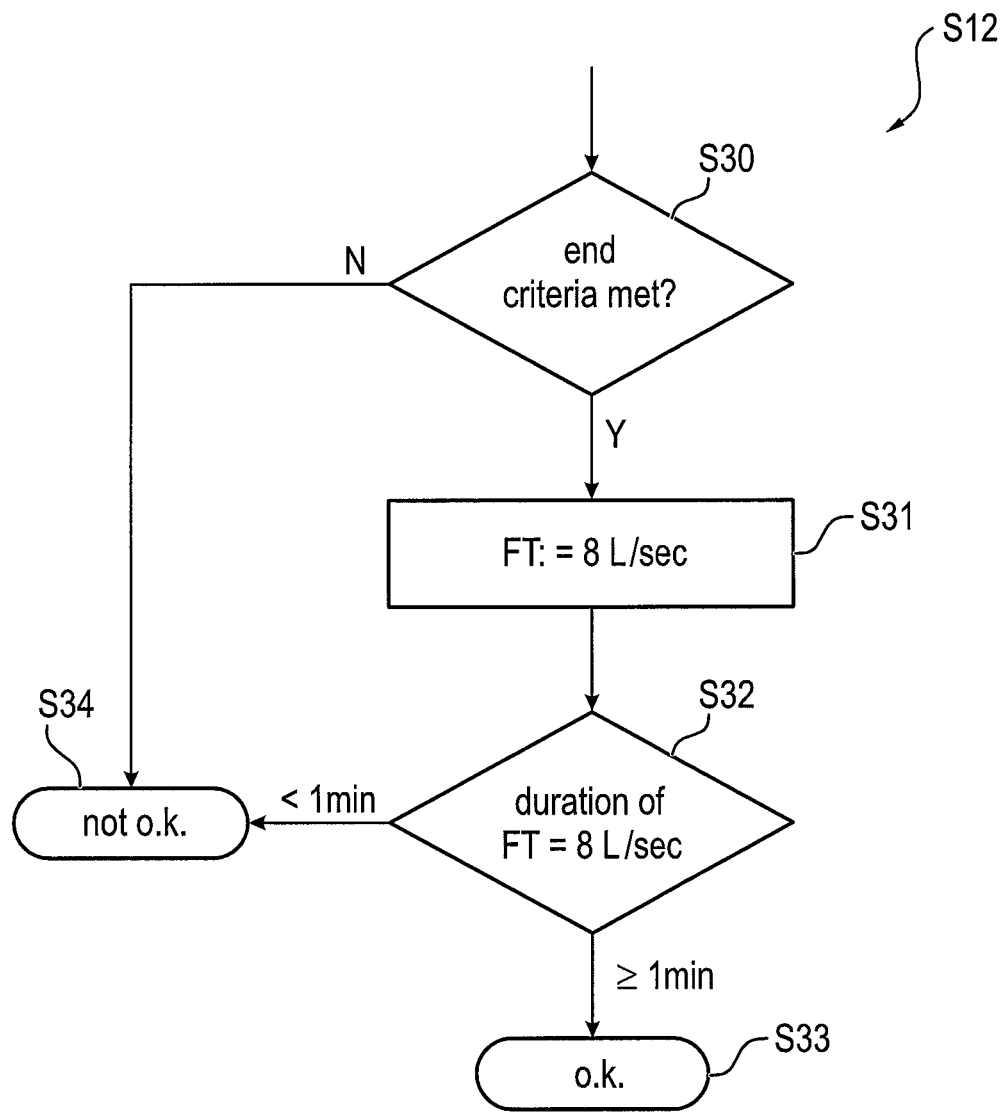
FIG. 6 is a flow diagram showing second partial steps of the process according to the present invention.

It will now be explained in detail how the desired operating state is detected within process step S12. Partial process steps of step S12 will be explained for this in more detail on the basis of FIG. 6.

It is checked in a partial process step S30 whether preset criteria or target values are met. FIG. 13 shows for this a Table T6, on the basis of which another preset concentration limit value can be determined for a carbon dioxide concentration etCO2G, and another preset volume limit value VTG as well as a preset desired pressure value ΔPG can be determined. These limit values or target values may preferably depend on a previously existing lung property ("lung mechanic"). A limit value is preferably also preset for a ventilation rate RrsponG.

It can now be checked on the basis of the tidal volume VT determined by the computer R of FIG. 3, of the end-expiratory carbon dioxide concentration etCO2, of the preset volume limit value VTG, of the preset concentration limit value etCO2G, of the current desired pressure value ΔP as well as of preset desired pressure value ΔPG whether the aforementioned target values are met. Further, a spontaneous breathing activity rate determined by the computer R is preferably also compared for this with the limit value RrsponG.

If the end criteria or the target values are met, the process is branched off in partial process step S30 to a partial process step S31. If the checking in partial process step S30 was negative, the process is branched off to partial process step S34, in which it is determined that the desired state of ventilation of the patient has not yet been reached.

If the desired state of ventilation of the patient was reached, the process is thus branched off from partial process step S30 to partial process step S31, the trigger threshold FT is then set to a preset value of preferably 8 L/sec there.

It is then checked in a next partial process step S32 whether the ventilation system or the ventilator has carried out the pressure support ventilation of the patient successfully for a preset time period, preferably 1 minute, with the preset threshold value of 8 L/sec, so that no warning signal indicating that a minimum ventilation rate RRmin was fallen below by the ventilation rate of the patient based on his spontaneous breathing activity was outputted. If this was not successful, the process is branched off from partial process step S32 to partial process step S34, in which it is detected that the desired state of ventilation of the patient is not present.

If it was determined that the patient was ventilated successfully in a pressure-supporting manner for the preset period, preferably 1 minute, taking the trigger threshold FT into consideration, the process is branched off from partial process step S32 to partial process step S33, and the presence of the desired operating state is detected in partial process step S33.

Even though some aspects were described in connection with a device, it is obvious that these aspects also represent a description of the corresponding process, so that a block or a component of a device can also be considered to be a corresponding process step or a feature of a process step. Analogously to this, aspects that were described in connection with or as a process step also represent a description of a corresponding block/step or detail or feature of a corresponding device and that the device or the corresponding computer is configured to carry out the process step.

The computer R shown in FIG. 3 can be considered to be at least one computer. The at least one computer R may also be embodied by a combination of a plurality of computers, preferably by the use of software in conjunction with hardware. Depending on certain implementation requirements, exemplary embodiments of the present invention may be implemented in hardware and/or in software. The implementation may also be carried out with the use of a digital storage medium, for example, a floppy disk, a DVD, a Blu-Ray disk, a CD, a ROM, a PROM, an EPROM, an EEPROM or a FLASH memory, a hard drive or another magnetic or optical memory, on which electronically readable control signals are stored, which can or do interact with a programmable component such that the particular process is carried out.

A programmable hardware component may be formed by a processor, a computer processor (CPU=Central Processing Unit), a graphics processor (GPU=Graphics Processing Unit), a computer, a computer system, an application-specific integrated circuit (ASIC=Application-Specific Integrated Circuit), an integrated circuit (IC=Integrated Circuit), a System on Chip (SOC), a programmable logic component or a field-programmable gate array with a microprocessor (FPGA=Field Programmable Gate Array).

The digital storage medium may therefore be machine- or computer-readable. Some exemplary embodiments consequently comprise a data storage medium, which has electronically readable control signals, which are capable of interacting with a programmable computer system or with a programmable hardware component such that one of the processes being described here is carried out. An exemplary embodiment is consequently a data storage medium (or a digital storage medium or a computer-readable medium), on which the program for carrying out one of the processes being described here is recorded.

Exemplary embodiments of the present invention may generally be implemented as program, firmware, computer program or computer program product with a program code or as data, wherein the program code or the data act so as to carry out one of the processes when the program is running on a processor or on a programmable hardware component. The program code or the data may also be stored, for example, on a machine-readable medium or data storage medium. The program code or the data may occur, among other things, as source code, machine code or byte code as well as as other intermediate code.

A further exemplary embodiment is, furthermore, a data stream, a signal sequence or a sequence of signals, which data stream or sequence represents the program for carrying out one of the processes described herein. The data stream, the signal sequence or the sequence of signals may be configured, for example, such as to be transferred via a data communication link, for example, via the Internet or another network. Exemplary embodiments are thus also signal sequences representing data, which are suitable for transmission via a network or a data communication link, wherein the data represent the program.

A program according to an exemplary embodiment may implement one of the processes during its execution, for example, by reading storage locations or by writing a datum or a plurality of data into these, wherein switching operations or other operations are optionally brought about in transistor structures, in amplifier structures or in other electrical, optical, magnetic components or components operating according to another principle of action. Data, values, sensor values or other information can correspondingly be detected, determined or measured by reading a storage location. A program can therefore detect, determine or measure variables, values, measured variables and other information by reading one or more storage locations as well as bring about, prompt or carry out an action as well as actuate other devices, machines and components by writing to one or more storage locations.

While specific embodiments of the invention have been shown and described in detail to illustrate the application of the principles of the invention, it will be understood that the invention may be embodied otherwise without departing from such principles.

The invention claimed is:

1. An anesthesia ventilator for automated ventilation of a patient, the anesthesia ventilator comprising:
an expiratory port and an inspiratory port for connecting a ventilation tube for supplying a breathing gas to the patient;
a breathing gas delivery unit;
at least one breathing gas sensor for detecting an anesthetic gas concentration;
at least one pressure sensor for detecting a pressure of the breathing gas;
at least one computer, wherein the at least one computer is configured to:
actuate the breathing gas delivery unit as a function of the detected pressure and of a preset desired pressure value; and
perform an adaptation of the desired pressure value as a function of the detected anesthetic gas concentration.

2. An anesthesia ventilator in accordance with claim 1, wherein the at least one computer is further configured to:
determine a mean alveolar anesthetic gas concentration as well as an end-expiratory anesthetic gas concentration on the basis of the detected anesthetic gas concentration; and
perform the adaptation of the desired pressure value as a function of the determined mean alveolar anesthetic gas concentration as well as a function of the determined end-expiratory anesthetic gas concentration.

3. An anesthesia ventilator in accordance with claim 1, further comprising:
at least one volume flow sensor for detecting a volume flow of the breathing gas, the at least one breathing gas sensor being configured for detecting a carbon dioxide concentration in the breathing gas, wherein:
the at least one computer is further configured to perform the adaptation of the desired pressure value as a function of the detected volume flow and as a function of the detected carbon dioxide concentration.

4. An anesthesia ventilator in accordance with claim 3, wherein the at least one computer is further configured to:
determine a tidal volume fed to the patient on the basis of the detected volume flow;
determine an end-expiratory carbon dioxide concentration on the basis of the detected carbon dioxide concentration; and
perform, furthermore, the adaptation of the desired pressure value as well as of a minimum ventilation rate as a function of:
the determined tidal volume;
an upper volume limit value;
and a lower volume limit value;
the determined end-expiratory carbon dioxide concentration;
an upper concentration limit value; and
a lower concentration limit value.

5. An anesthesia ventilator in accordance with claim 4, wherein the at least one computer is further configured to:
detect a desired operating state concerning the automated ventilation as a function of:
the determined tidal volume;
the determined end-expiratory carbon dioxide concentration;
another preset volume limit value;
another preset concentration limit value;
the current desired pressure value;
a preset desired pressure limit value; and
output, in case of detection, an output signal, which indicates the presence of the desired operating state, to a clinician.

6. An anesthesia ventilator in accordance with claim 1, wherein the at least one computer is further configured to actuate the breathing gas delivery unit such that the automated ventilation is carried out as a pressure support ventilation.

7. An anesthesia ventilator in accordance with claim 6, further comprising at least one volume flow sensor for detecting a volume flow of the breathing gas, wherein the at least one computer is further configured to:
detect an attempt at spontaneous breathing by the patient on the basis of the detected volume flow; and
carry out the pressure support ventilation with the use of the desired pressure value if an attempt at spontaneous breathing is detected.

8. An anesthesia ventilator in accordance with claim 7, wherein the at least one computer is further configured to control output of a warning signal as a function of detected attempts at spontaneous breathing and as a function of a presettable minimum ventilation rate.

9. A process for operating an anesthesia ventilator for automated ventilation of a patient, the process comprising the steps of:

feeding a breathing gas to the patient via an inspiratory port and returning the breathing gas via an expiratory port by operating a breathing gas delivery unit;

detecting an anesthetic gas concentration by means of at least one anesthetic gas sensor;

detecting a pressure of the breathing gas by means of at least one pressure sensor;

actuating the breathing gas delivery unit as a function of the detected pressure and of a preset desired pressure value by means of at least one computer;

adapting the desired pressure value as a function of the detected anesthetic gas concentration.

10. A process in accordance with claim 9, further comprising:

determining a mean alveolar anesthetic gas concentration as well as an end-expiratory anesthetic gas concentration on the basis of the detected anesthetic gas concentration signal; and performing the adaptation of the desired pressure value as a function of the determined mean alveolar anesthetic gas concentration as well as a function of the determined end-expiratory anesthetic gas concentration.

11. A process in accordance with claim 9, further comprising:

detecting a volume flow of the breathing gas;

detecting a carbon dioxide concentration in the breathing gas;

adapting the desired pressure value as a function of the detected volume flow and as a function of the detected carbon dioxide concentration.

12. A computer for an anesthesia ventilator for automated ventilation of a patient, wherein the computer is configured:

to detect an anesthetic gas concentration signal, which indicates an anesthetic gas concentration in a breathing gas;

to detect a pressure signal, which indicates a pressure of the breathing gas;

to provide an actuating signal for a breathing gas delivery unit, wherein the computer determines the actuating signal as a function of the detected pressure signal and of a preset desired pressure value; and to perform an adaptation of the desired pressure value as a function of the detected anesthetic gas concentration signal.

13. A computer in accordance with claim 12, wherein the computer is further configured to:

determine a mean alveolar anesthetic gas concentration as well as an end-expiratory anesthetic gas concentration on the basis of the detected anesthetic gas concentration; and perform the adaptation of the desired pressure value as a function of the determined mean alveolar anesthetic gas concentration as well as a function of the determined end-expiratory anesthetic gas concentration.

14. A computer in accordance with claim 12, wherein the computer is further configured to:

detect a volume flow of the breathing gas;

detect a carbon dioxide concentration in the breathing gas;

adapt the desired pressure value as a function of the detected volume flow and as a function of the detected carbon dioxide concentration.

15. A process for operating an anesthesia ventilator for automated ventilation of a patient, the process comprising the steps of:

detecting an anesthetic gas concentration signal, which indicates an anesthetic gas concentration in a breathing gas;

detecting a pressure signal, which indicates a pressure of the breathing gas;

providing an actuating signal for a breathing gas delivery unit as a function of the detected pressure signal and of a preset desired pressure value; and adapting the desired pressure value as a function of the detected anesthetic gas concentration signal.

16. A process in accordance with claim 15, wherein the process is carried out with a computer program on at least one computer.

17. A process in accordance with claim 15, further comprising:

determining a mean alveolar anesthetic gas concentration as well as an end-expiratory anesthetic gas concentration on the basis of the detected anesthetic gas concentration signal; and performing the adaptation of the desired pressure value as a function of the determined mean alveolar anesthetic gas concentration as well as a function of the determined end-expiratory anesthetic gas concentration.

18. A process in accordance with claim 15, further comprising:

detecting a volume flow of the breathing gas;

detecting a carbon dioxide concentration in the breathing gas;

adapting the desired pressure value as a function of the detected volume flow and as a function of the detected carbon dioxide concentration.

* * * * *